United States Patent
Proia

(10) Patent No.: US 11,154,538 B2
(45) Date of Patent: Oct. 26, 2021

(54) COMBINATION THERAPY FOR TREATMENT OF OVARIAN CANCER

(71) Applicant: SYNTA PHARMACEUTICALS CORP., Lexington, MA (US)

(72) Inventor: David Proia, Newton, MA (US)

(73) Assignee: Synta Pharmaceuticals Corporation, Lexington, MA (US)

( * ) Notice: Subject to any disclaimer, the term of this patent is extended or adjusted under 35 U.S.C. 154(b) by 0 days.

(21) Appl. No.: 16/080,752

(22) PCT Filed: Feb. 28, 2017

(86) PCT No.: PCT/US2017/019843
§ 371 (c)(1),
(2) Date: Aug. 29, 2018

(87) PCT Pub. No.: WO2017/151554
PCT Pub. Date: Sep. 8, 2017

(65) Prior Publication Data
US 2019/0060285 A1 Feb. 28, 2019

Related U.S. Application Data

(60) Provisional application No. 62/301,225, filed on Feb. 29, 2016.

(51) Int. Cl.
| | | |
|---|---|---|
| A61K 31/5377 | (2006.01) | |
| A61K 33/243 | (2019.01) | |
| A61P 35/00 | (2006.01) | |
| A61K 31/4196 | (2006.01) | |
| A61K 45/06 | (2006.01) | |
| A61K 31/519 | (2006.01) | |
| C12Q 1/6886 | (2018.01) | |

(52) U.S. Cl.
CPC ........ *A61K 31/4196* (2013.01); *A61K 31/519* (2013.01); *A61K 45/06* (2013.01); *C12Q 1/6886* (2013.01); *C12Q 2600/106* (2013.01); *C12Q 2600/156* (2013.01)

(58) Field of Classification Search
CPC ... A61K 31/5377; A61K 33/243; A61P 35/00; C12N 15/8213; C12N 15/902; C12N 15/1082; A01K 2217/07; A01K 2217/15
See application file for complete search history.

(56) References Cited

U.S. PATENT DOCUMENTS

| 7,825,148 B2 | 11/2010 | Ying et al. |
| 2014/0255348 A1 | 9/2014 | Proia |

FOREIGN PATENT DOCUMENTS

| JP | 2011503071 A | 1/2011 |
| WO | 2012162372 A1 | 11/2012 |
| WO | 2012162584 A1 | 11/2012 |
| WO | 2014138101 A1 | 9/2014 |
| WO | 2014189937 A1 | 11/2014 |
| WO | WO-2016025958 A1 | 2/2016 |

OTHER PUBLICATIONS

Stecklein et al. BRCA1 and hsp90 cooperate in homologous and non-homologous DNA double-strand-break and G2/M checkpoint activation. PNAS, Aug. 21, 2012, vol. 109, No. 34.*
Jhaveri et al. Ganetespib: research and clinical development. OncoTargets and Therapy, 2015: 8, 1849-1858.*
Choi et al. Sublethal concentrations of 17-AAG suppress homologous recombination DNA repair and enhance sensitivity to carboplatin and olaparib in HR proficient ovarian cancer cells. Oncotarget, vol. 5, No. 9, 2014.*
Mangioni et al. Randomized trial in advanced ovarian cancer comparing cisplatin and carboplatin. J. Natl. Cancer Inst. 81: 1464-1471, 1989.*
Wilcoxen et al. Use of homologous recombination deficiency (HRD) score to enrich for niraparib sensitive high grade ovarian tumors. Journal of Clinical Oncology, 33, No. 15, May 20, 2015.*
Timms et al. Association of BRCA1/2 defects with genomic scores predictive of DNA damage repair deficiency among breast cancer subtypes. Breast Cancer Research, 2014, 16: 475.*
Abkevich et al., Patterns of genomic loss of heterozygosity predict homologous recombination repair defects in epithelial ovarian cancer, Br J Cancer,107(10):1776-1782 (Nov. 2012).
Birkbak et al., Telomeric allelic imbalance indicates defective DNA repair and sensitivity to DNA-damaging agents, Cancer Discov, 2(4):366-375 (Apr. 2012).
Fojo et al., "Mechanisms of Resistance to PARP Inhibitors—Three and Counting" Cancer Discov, 3(1):20-23 (Jan. 2013).
Hirshfield et al., Triple-negative breast cancer: molecular subtypes and targeted therapy, Curr Opin Obstet Gynecol, 26:34-40 (Feb. 2014).
Lapenna et al., "Cell cycle kinases as therapeutic targets for cancer," Nat Rev Drug Discov, 8(7):547-566 (Jul. 2009).
Ledermann et al., "Homologous recombination deficiency and ovarian cancer," Eur J Cancer, 60:49-58 (Jun. 2016).
Ray-Coquard et al., "Part I of GANNET53: A multicenter phase I/II trial of the Hsp90 inhibitor ganetespib (G) combined with weekly paclitaxel (P) in women with high-grade serous, high-grade endometrioid, or undifferentiated, platinum-resistant epithelial ovarian, fallopian tube or primary peritoneal cancer," J Clin Oncology, 33(15):5578 (May 2015).
Timms et al., "Association of BRCA1/2 defects with genomic scores predictive of DNA damage repair deficiency among breast cancer subtypes," Breast Cancer Res, 16(6):475 (Dec. 2014).
International Search Report and Written Opinion for International Application No. PCT/US2017/019843, dated May 24, 2017 (11 pages).

(Continued)

*Primary Examiner* — Theodore R. Howell
(74) *Attorney, Agent, or Firm* — Dechert LLP; Andrea L. C. Reid; Joseph W. Arico

(57) ABSTRACT

This invention relates to methods of treating a patient with ovarian cancer having deficiencies in homologous recombination (HR) comprising administering to the patient (i) an effective amount of ganetespib, or a pharmaceutically acceptable salt thereof; and (ii) an effective amount of a DNA-damaging or repair-inhibiting agent.

7 Claims, No Drawings

(56) References Cited

OTHER PUBLICATIONS

Pulliam et al., "An Effective Epigenetic-PARP Inhibitor Combination Therapy for Breast and Ovarian Cancers Independent of BRCA Mutations," Clin Cancer Res, 24(13):3163-3175 (Jul. 2018).
Liu et al., "Network analysis identifies an HSP90-central hub susceptible in ovarian cancer," Clin Cancer Res. 2013; 19(18):5053-67.
Stordal et al., "BRCA1/2 mutation analysis in 41 ovarian cell lines reveals only one functionally deleterious BRCA1 mutation," Mol Oncol. 2013; 7(3):567-79.

* cited by examiner

COMBINATION THERAPY FOR TREATMENT OF OVARIAN CANCER

CROSS-REFERENCE TO RELATED APPLICATIONS

This application is a § 371 national stage of PCT International Application No. PCT/US2017/019843, filed Feb. 28, 2017, claiming the benefit of U.S. Provisional Application No. 62/301,225, filed Feb. 29, 2016, the contents of each of which are hereby incorporated by reference in their entirety.

FIELD OF THE INVENTION

This invention relates to a combination therapy comprising ganetespib and a DNA-damaging or repair-inhibiting agent to treat ovarian cancer.

BACKGROUND OF THE INVENTION

Ovarian cancer accounts for about 3% of cancers among women. It begins in the ovaries. The ovaries are made up of 3 main kinds of cells. Each type of cell can develop into a different type of tumor:
  Epithelial tumors originates in the layer of cells that cover the outer surface of the ovary. About 90 percent ovarian tumors are epithelial cell tumors.
  Germ cell tumors start from the cells that produce the eggs (ova).
  Stromal tumors start from structural tissue cells that hold the ovary together and produce the female hormones estrogen and progesterone.

There remains a need in the art for novel therapies capable of effectively and reliably treating ovarian cancer, in particular, epithelial ovarian cancer. The present invention addresses this and other such needs.

SUMMARY OF THE INVENTION

One embodiment of the invention is a method of treating a patient with ovarian cancer having deficiencies in homologous recombination (HR) comprising administering to the patient (i) an effective amount of ganetespib, or a pharmaceutically acceptable salt thereof; and (ii) an effective amount of a DNA-damaging or repair-inhibiting agent. In one embodiment, the patient with ovarian cancer having deficiencies in homologous recombination (HR) has a homologous recombination deficiency (HRD) score of greater than 40, preferably greater than 42.

Another embodiment of the invention is a method of treating a patient with ovarian cancer having proficient homologous recombination (HR), comprising administering to the patient (i) an effective amount of ganetespib, or a pharmaceutically acceptable salt thereof; and (ii) an effective amount of a DNA-damaging or repair-inhibiting agent.

The present invention is also directed to a method of treating a patient with ovarian cancer, comprising the steps of:
  a) screening the ovarian cancer of the patient to assess whether the cancer is HR deficient or HR proficient;
  b) if the ovarian cancer is HR deficient, administering to the patient an effective amount of Ganetespib or a pharmaceutically acceptable salt thereof and an effective amount of a DNA damaging or repair inhibiting agent.

In one embodiment of the above-described method, wherein if the cancer is HR proficient, treating the patient with an anti-cancer therapy other than Ganetespib or a pharmaceutically acceptable salt thereof.

In one embodiment, the invention provides a method according to any one of the previous embodiments, wherein the DNA-damaging or repair-inhibiting agent is selected from the group consisting of a PARP inhibitor, a platin, a topoisomerase I inhibitor, a topoisomerase II inhibitor, and an inhibitor of DNA checkpoint proteins including WEE1, CHK1, CHK2, CDK1, CDK2, ATM, and ATR.

In one embodiment, the invention provides a method according to any one of the previous embodiments, wherein the ovarian cancer has BRCA reversion, methylation reversal of BRCA, an N terminal BRCA missense mutation or other mutations in BRCA that yield a functional protein, expression of drug transporters, BRCA mutant proteins reliant on HSP90 for stability and function, amplification of Cyclin E1, or desmoplastic stroma.

In one embodiment, the invention provides a method according to any one of the previous embodiments, wherein the ovarian cancer is epithelial ovarian cancer.

In one embodiment, the invention provides a method according to any one of the previous embodiments, wherein the DNA-damaging or repair-inhibiting agent is a PARP inhibitor, and the PARP inhibitor is niraparib, iniparib, talazoparib, olaparib, rucaparib, veliparib, or CEP-9722.

In one embodiment, the invention provides a method according to any one of the previous embodiments, wherein the DNA-damaging or repair-inhibiting agent is a topoisomerase I inhibitor, and the topoisomerase I inhibitor is irinotecan, topotecan, camptothecin, or lamellarin D.

In one embodiment, the invention provides a method according to any one of the previous embodiments, wherein the DNA-damaging or repair-inhibiting agent is a topoisomerase II inhibitor, and the topoisomerase II inhibitor is etoposide (VP-16), teniposide, doxorubicin, daunorubicin, mitoxantrone, amsacrine, ellipticine, aurintricarboxylic acid, HU-331, ICRF-187, ICRF-193, or mitindomide.

In one embodiment, the invention provides a method according to any one of the previous embodiments, wherein the DNA-damaging or repair-inhibiting agent is a platin, and the platin is cisplatin, carboplatin, oxaliplatin, satraplatin, picoplatin, nedaplatin, triplatin, or lipoplatin.

In one embodiment, the invention provides a method according to any one of the previous embodiments, wherein the DNA-damaging or repair-inhibiting agent is a WEE1 inhibitor, and the WEE1 inhibitor is AZD-1775.

In one embodiment, the invention provides a method according to any one of the previous embodiments, wherein the DNA-damaging or repair-inhibiting agent is a CHK1 and/or 2 inhibitor, and the CHK1 and/or 2 inhibitor is AZD7762, LY2603618, MK-8776, CHIR-124, or PF-477736.

In one embodiment, the invention provides a method according to any one of the previous embodiments, wherein the DNA-damaging or repair-inhibiting agent is a CDK1 and/or 2 inhibitor, and the CDK1 and/or 2 inhibitor is rosovitine, SNS-032, dinaciclib, flavopiridol, AT7519, purvalanol A, RO-3306, SU9516, XL413, NU6027, P276-00, AZD5438, PHA-793887, JNJ-7706621, BMS-265246, milciclib, MK-8776, or R547.

In one embodiment, the invention provides a method according to any one of the previous embodiments, wherein the DNA-damaging or repair-inhibiting agent is a ATM and/or ATR inhibitor, and the ATM and/or ATR inhibitor is dactolisib, KU-55933, KU-60019, VE-821, wortmannin, AZD6738, CP-466722, torin 2, ETP-46464, CGK 733, AZ20, VE-822, schisandrin B, or chloroquine phosphate.

In one embodiment, the present invention provides the use of ganetespib, or a pharmaceutically acceptable salt thereof, for the manufacture of a medicament for the treatment of a patient in combination with a DNA-damaging or repair-inhibiting agent, the patient has (i) ovarian cancer having deficiencies in homologous recombination (HR); (ii) ovarian cancer having proficient homologous recombination (HR); or (iii) epithelial ovarian cancer. In a specific embodiment, the DNA-damaging or repair-inhibiting agent is selected from the group consisting of a PARP inhibitor, a platin, a topoisomerase I and/or II inhibitor, and an inhibitor of DNA checkpoint proteins including WEE1, CHK1, CHK2, CDK1, CDK2, ATM, and ATR.

In another embodiment, the present invention provides ganetespib or a pharmaceutically acceptable salt thereof for use in the treatment of ovarian cancer in a patient in need thereof, in combination with a DNA-damaging or repair-inhibiting agent selected from the group consisting of a PARP inhibitor, a platin, a topoisomerase I and/or II inhibitor, and an inhibitor of DNA checkpoint proteins including WEE1, CHK1, CHK2, CDK1, CDK2, ATM, and ATR. In a specific embodiment, the ovarian cancer has deficiencies in homologous recombination (HR). In another specific embodiment, the ovarian cancer has proficient homologous recombination (HR). In yet another specific embodiment, the ovarian cancer is PARP inhibitor-resistant ovarian cancer. In still another specific embodiment, the ovarian cancer is epithelial ovarian cancer.

DETAILED DESCRIPTION OF THE INVENTION

Homologous recombination is a type of genetic recombination used to repair DNA breaks. BRCA1 and BRCA2 are well known as critical proteins in the process of homologous recombination and many other proteins have been shown to participate in the repair process including ATM, ATR, p53, CHEK2, BARD1, RAD51. Deficiencies in homologous recombination have been strongly linked to cancer formation in humans. Cancer cells that have lost normal BRCA1 or BRCA2 activity, hence considered homologous recombination deficient, are critically dependent on other parts of the repair pathway to avoid repair catastrophe.

Deficiency in homologous recombination can be caused by lost normal BRCA1 or BRCA2 activity, which includes, but not limited to, BRCA reversion, methylation reversal of BRCA, an N terminal BRCA missense mutation or other mutations in BRCA that yield a functional protein, expression of drug transporters, BRCA mutant proteins reliant on HSP90 for stability and function, amplification of Cyclin E1, and desmoplastic stroma.

Ovarian cancers with homologous recombination deficiency (HRD) have been shown to benefit from therapy with DNA-damaging agents, such as platinum and PARP-inhibitors. The homologous recombination deficiency can be evaluated and determined by a HRD score. The HRD score is calculated from three components which reflect different types of tumor genome rearrangements. The three individual components are: 1) Loss of heterozygosity (LOH), which are regions of intermediate size (>15 Mb and <whole chromosome) in the tumor genome; 2) Large-scale State Transitions (LST), which are chromosome breaks (translocations, inversions or deletions) in adjacent segments of DNA at least 10 Mb; and 3) Telomeric Allelic Imbalance (TAI), which are defined as the number of regions with allelic imbalance which extend to the sub-telomere but do not cross the centromere. The HRD Score is the unweighted sum of LOH, TAI and LST measurements on a scale from 0-100, which can be calculated by the following formula.

$$HRD\text{-model}=0.11 \times HRD\text{-}LOH+0.25 \times HRD\text{-}TAI+0.12 \times HRD\text{-}LST$$

The detailed description as to how to calculate the HRD score can be found in Timms et al. Breast Cancer Research (2014) 16:475, the entire contents of which is incorporated herein by reference. The whole procedure is described in the Example Section.

When the HRD score is greater than 40, preferably greater than 42, it is considered that a patient has deficiency of homologous recombination. Vice versa, when the HRD score is less than 40, it is considered that a patient has proficiency of homologous recombination.

It is believed that ganetespib, a second generation HSP90 inhibitor unrelated to the ansamycin class of HSP90 inhibitors, will enhance the activity of PARP inhibitors or other DNA damaging therapeutics in ovarian cancers with deficiencies (or proficiencies) in homologous recombination in part by impairing the multitude of DNA repair proteins it chaperones.

Ganetespib (3-(2,4-dihydroxy-5-isopropyl-phenyl)-4-(1-methyl-indol-5-yl)-5-hydroxy-[1,2,4] triazole) is represented by the following structural formula:

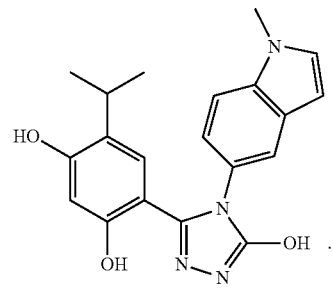 [SMILES: CC(C)c1cc(-c2nnc(O)n2-c2ccc3c(ccn3C)c2)c(O)cc1O]

Synthetic preparations for Ganetespib are provided in U.S. Pat. No. 7,825,148, the entire teachings of which are incorporated herein by reference.

A DNA-damaging or repair-inhibiting agent refers to an agent that causes DNA damages. It is targeted at some of the key regulatory proteins involved in the DNA repair process. The DNA repair process in mammalian cells is a multi-pathway mechanism that protects cells from the plethora of DNA damaging agents that are known to attack nuclear DNA. The majority of current anticancer therapies rely on this ability to create DNA lesions, leading to apoptosis/cell death. A cells natural ability to repair such DNA damage is a major cause of resistance to these existing antitumour agents. It seems logical, therefore, that by modulating these repair mechanisms, greater killing effect to anticancer agents would occur.

A DNA-damaging or repair-inhibiting agent includes, but not limited to, a PARP inhibitor, a platin, a topoisomerase I and/or II inhibitor, and an inhibitor of DNA checkpoint proteins including WEE1, CHK1, CHK2, CDK1, CDK2, ATM, and ATR.

PARP Inhibitors

PARPs are a family of proteins that can detect DNA damage, bind to DNA single strand breaks (SSBs), recruit DNA repair proteins, and drive the repair process. The PARP family of proteins in humans includes PARP1 and PARP2.

By inhibiting PARP activity with small molecule drugs (i.e., PARP inhibitors), unrepaired SSBs can lead to more deleterious double strand breaks (DSBs), which require homologous recombination (HR) for repair. Thus, drugs that inhibit PARP cause multiple double strand breaks to form in this way. In tumors with BRCA1, BRCA2 or PALB2 mutations, these double strand breaks cannot be efficiently repaired, leading to the death of the tumor cells. Yet, normal cells don't replicate their DNA as often as cancer cells. Also, the normal cells lack any mutated BRCA1 or BRCA2, and thus still have homologous repair operating, which allows them to survive the inhibition of PARP.

The PARP inhibitor can be used in the present invention includes, but not limited to, niraparib, iniparib, talazoparib, olaparib, rucaparib, veliparib, and CEP-9722.

Platins

A platin refers to a platinum-based antineoplastic drug, which is a chemotherapeutic agent to treat cancer. A platin is a coordination complex of platinum. Platinum-based antineoplastic drugs cause crosslinking of DNA as mono-adduct, interstrand crosslinks, intrastrand crosslinks or DNA protein crosslinks. Mostly they act on the adjacent N-7 position of guanine, forming 1, 2 intrastrand crosslink. The resultant crosslinking inhibit DNA repair and/or DNA synthesis in cancer cells. Examples of platins include cisplatin, carboplatin, oxaliplatin, satraplatin, picoplatin, nedaplatin, triplatin, and lipoplatin.

Topoisomerase Inhibitors

Topoisomerase inhibitors are agents designed to interfere with the action of topoisomerase enzymes, which include topoisomerase I and II. Topoisomerase are enzymes that control the changes in DNA structure by catalyzing the breaking and rejoining of the phosphodiester backbone of DNA strands during the normal cell cycle.

Human DNA topoisomerase I (Top1) is an essential enzyme that relaxes DNA supercoiling during replication and transcription. Top1 generates DNA single-strand breaks that allow rotation of the cleaved strand around the double helix axis. Top1 also relegates the cleaved strand to reestablish intact duplex DNA. The Top1-DNA intermediates, known as cleavage complexes, are transient and at low levels under normal circumstances. However, treatment with Top1 inhibitors, such as the camptothecins, stabilize the cleavable complexes, prevent DNA relegation and induce lethal DNA strand breaks. Cancer cells are selectively sensitive to the generation of these DNA lesions. The topoisomerase I inhibitor can be used in the present invention includes, but not limited to, irinotecan, topotecan, camptothecin, or lamellarin D.

Type II topoisomerases cut both strands of the DNA helix simultaneously in order to manage DNA tangles and supercoils. They use the hydrolysis of ATP, unlike Type I topoisomerase. In this process, these enzymes change the linking number of circular DNA by ±2. The topoisomerase II inhibitor can be used in the present invention includes, but not limited to, etoposide (VP-16), teniposide, doxorubicin, daunorubicin, mitoxantrone, amsacrine, ellipticine, aurintricarboxylic acid, HU-331, ICRF-187, ICRF-193, and mitindomide.

Inhibitor of DNA Checkpoint Proteins

After DNA damage, cell cycle checkpoints are activated. Checkpoint activation pauses the cell cycle and gives the cell time to repair the damage before continuing to divide. DNA damage checkpoints occur at the DNA synthesis G1/S and G2/M phases. An intra-S checkpoint also exists. Checkpoint activation is controlled by two master kinases, ATM (Ataxia telangiectasia mutated) and ATR (ataxia telangiectasia and RAD3-related protein). ATM responds to DNA double-strand breaks and disruptions in chromatin structure, whereas ATR primarily responds to stalled replication forks.

The ATM-ATR cascade is activated within minutes of a DNA damage alarm. Both ATM and ATR can phosphorylate and activate the transcription factor p53, either directly or by means of prior activation of checkpoint kinase 2 (CHK2). Among the genes induced by p53 is the cyclin-dependent kinase 2 (CDK2) inhibitor p21 (also known as CDKN1A and CIP1), the activity of which prevents damaged cells from entering the DNA synthesis (S) phase. Also, damaged cells that have already passed the transition from the first gap (G1) phase to S phase can be halted through the activation of another ATM-ATR effector, CHK1, which phosphorylates the dual-specificity phosphatase CDC25C, providing a signal that induces its sequestration in the cytoplasm. Because CDC25C is responsible for removing two inhibitory phosphates from CDK1, its inactivation prevents the cell from entry into the mitosis (M) phase. Cell cycle arrest in G1, S or G2 phase is maintained until DNA integrity is restored. If lesions are irreparable, programmed cell death is induced by the ATM-ATR signalling pathway. The ATM-CHK2 pathway predominantly regulates the G1 checkpoint, whereas the ATR-CHK1 pathway predominantly regulates the S and G2 checkpoints, although there is crosstalk between these pathways. In most human cancers, however, the function of the DNA damage checkpoint in G1 is impaired owing to mutations in p53 or the gene encoding the retinoblastoma protein (RB1). Treatment of these tumor cells with DNA-damaging agents, such as ionizing radiation and DNA-targeting drugs, results in S or G2 checkpoint-mediated arrest. See Lapenna et al., "Cell cycle kinases as therapeutic targets for cancer" Nature Reviews Drug Discovery 2009 (8), 547-566.

In sum, DNA damage checkpoint is a signal transduction pathway that blocks cell cycle progression in G1, G2 and metaphase and slows down the rate of S phase progression when DNA is damaged. It leads to a pause in cell cycle allowing the cell time to repair the damage before continuing to divide.

The inhibitor of DNA checkpoint proteins can be used in the present invention includes, but not limited to, WEE1, CHK1, CHK2, CDK1, CDK2, ATM, and ATR.

The WEE1 inhibitor include, but not limited to, AZD-1775.

The CHK 1 and/or 2 inhibitors include, but not limited to, AZD7762, LY2603618, MK-8776, CHIR-124, and PF-477736.

The CDK 1 and/or 2 inhibitors include, but not limited to, rosovitine, SNS-032, dinaciclib, flavopiridol, AT7519, purvalanol A, RO-3306, SU9516, XL413, NU6027, P276-00, AZD5438, PHA-793887, JNJ-7706621, BMS-265246, milciclib, MK-8776, and R547.

The ATM and/or ATR inhibitors include, but not limited to, dactolisib, KU-55933, KU-60019, VE-821, wortmannin, AZD6738, CP-466722, torin 2, ETP-46464, CGK 733, AZ20, VE-822, schisandrin B, and chloroquine phosphate.

As with other therapies, resistance to PARP inhibitors in advanced disease is almost inevitable. Several mechanisms for PARP inhibitors resistance have been described including mutations in the BRCA promoter or gene that restore protein functionality, for example, the functionality of homologous recombination, which is previously deficient due to the defect that BRCA deletion confers. See Fojo et al., "Mechanisms of Resistance to PARP Inhibitors—Three and Counting" Cancer Discovery, 2013 (3) 20-23. Inhibiting HSP90 may be a useful strategy to combat this mechanism of resistance or to treat recurrent or refractory disease.

As such, the present invention is also directed to a method of treating a patient with PARP inhibitor-resistant ovarian cancer. The PARP inhibitor-resistant ovarian cancer has BRCA reversion, methylation reversal of BRCA, an N terminal BRCA missense mutation or other mutations in BRCA that yield a functional protein, expression of drug transporters, BRCA mutant proteins reliant on HSP90 for stability and function, amplification of Cyclin E1, or desmoplastic stroma. In one embodiment, the PARP inhibitor-resistant ovarian cancer is HR-deficient PARPi-resistant epithelial ovarian cancer.

As used herein, the term "pharmaceutically acceptable salt," is a salt formed from, for example, a basic group on Ganetespib (e.g., the indolyl nitrogen) and a pharmaceutically acceptable acid, i.e., an acid addition salt. Illustrative acid addition salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from an acidic functional group on Ganetespib (e.g., a phenolic group) and a pharmaceutically acceptable base. Suitable bases include, but are not limited to, hydroxides and alkoxides of alkali metals such as sodium, potassium, and lithium. "Pharmaceutically acceptable" means suitable for use in humans.

"Effective amount" refers to an amount of Ganetespib (or a pharmaceutically acceptable salt thereof), a DNA-damaging or repair-inhibiting agent (selected from the group consisting of a PARP inhibitor, a platin, a topoisomerase I and/or II inhibitor, and an inhibitor of DNA checkpoint proteins including WEE1, CHK1, CHK2, CDK1, CDK2, ATM, and ATR), alone or in combination, which is sufficient to reduce or ameliorate the severity, symptoms or progression of ovarian cancer, reduce the advancement of ovarian cancer, cause the regression of ovarian cancer or reduce the likelihood of recurrence or progression of a symptom associated with ovarian cancer without causing unacceptable side effects. The precise amount of Ganetespib (or a pharmaceutically acceptable salt thereof), and a DNA-damaging or repair-inhibiting agent administered to a patient will depend on the mode of administration, the type and severity of the ovarian cancer and on the characteristics of the patient, such as general health, age, sex, body weight and tolerance to the drugs. The skilled artisan will be able to determine appropriate dosages depending on these and other factors. Suitable dosages are known for Ganetespib (or a pharmaceutically acceptable salt thereof), a DNA-damaging or repair-inhibiting agent and can be adjusted by the skilled artisan according to the factors described above.

In the disclosed methods, Ganetespib (or a pharmaceutically acceptable salt thereof) is administered by any suitable route in any suitable pharmaceutical formulation, as described in U.S. Pat. No. 7,825,148. In one embodiment, Ganetespib (or a pharmaceutically acceptable salt thereof) is administered at an intravenous infusion via peripheral intravenous access. In one embodiment, Ganetespib (or a pharmaceutically acceptable salt thereof) is administered over a period of 15 minutes to three hours. Alternatively, Ganetespib (or a pharmaceutically acceptable salt thereof) is administered over a period of 30 minutes to two hours. Alternatively, Ganetespib (or a pharmaceutically acceptable salt thereof) is administered over a one hour period. Preferably, the DNA-damaging or repair-inhibiting agent is also administered by infusion.

The invention can be understood more fully by reference to the following illustrative examples, which are intended to exemplify non-limiting embodiments of the invention.

EXAMPLES

Example 1

DNA is extracted from formalin fixed paraffin-embedded (FFPE) tumor tissue and used to create libraries that are hybridized to a custom Agilent SureSelect capture panel carrying probes for single nucleotide polymorphism sites distributed across the human genome, as well as probes targeting genes involved in DNA repair, including BRCA1 and BRCA2. The captured and enriched DNA is sequenced on an Illumina HiSeq 2500 sequencer. Sequences covering SNP positions are used to generate allelic imbalance profiles. Measures of genomic instability, including determination of a HRD score (integer value of 0-100), are calculated using allelic imbalance profiles and determination of loss of heterozygosity by ASCN.

Genomic DNA (gDNA) is used for the SureSelect XT capture method. Briefly gDNA is sheared on a Covaris E220 so that the peak size is between 150 and 200 nucleotides. Amplification of adapter-ligated library precedes an overnight hybridization at 65 degrees Celsius with the SureSelect biotinylated RNA library baits. Following hybridization between individual adapter-ligated libraries and the RNA library baits, index tags are added by amplification so that pooled barcoded samples could be run on the Illumina HiSeq2500 sequencer (Illumina, San Diego, Calif.).

Individual libraries are pooled depending on the desired sequencing coverage and type of sequencing run, e.g. Rapid Run mode and High Output mode. Generally 6 individual samples are pooled together for sequencing runs that underwent Rapid Run mode and 12 samples are pooled together for sequencing runs that underwent High Output mode. Individual sample libraries are combined such that each index-tagged sample would be present in equimolar amounts in the pool. For most purposes pools are made so that each library is at a final concentration of 10 nM. From here the standard Illumina Sequencing protocol is followed to denature and dilute the pooled libraries to 7 pM for loading on Rapid and High Output flow cells.

BRCA1 and BRCA2 Mutation Screening

Sequence reads generated on the HiSeq2500 are trimmed at both the start and end to remove low quality bases that could generate spurious variant calls. Sequence trimming is largely performed according to the BWA program's trimming algorithm (Burrows and Wheeler, 1994; Li and Durbin, 2009). For more detail see http://solexaqa.sourceforge.net/. Phred value 20 is used as a threshold for trimming at the start of sequences and 30 for trimming at the end. These thresholds are derived empirically. It is expected that the sequence quality will deteriorate towards the end of a read, so we use a higher threshold at the end of sequences.

For each read an in-house implementation of the Burrow Wheeler Transform algorithm (Burrows and Wheeler, 1994) is executed which performs a search of all exons in our database to determine the matching exon for each read.

To call variants each read is aligned with the expected wildtype sequence of the exon. This alignment is a pairwise alignment performed by JAligner (http://jaligner.sourceforge.net/). Any differences represent variants. Variant calls from all reads for a sample are compiled in order to calculate the frequencies of all identified variants.

Large Rearrangement Detection

For large rearrangement detection the number of reads N that mapped back to each base is normalized ($N_{norm}$) using the total number of mapped back reads across all genes and SNP locations. A median normalized read count value $N_{med}$ in a large set of samples is determined for each base. Centered normalized read counts, defined as $N_{cent}=N_{norm}/N_{med}$, are reviewed to detect large rearrangements encompassing one or more exons. The CV of centered normalized read counts for the exon 11 (largest exon) of both BRCA1 and BRCA2 is determined. If CV is below 0.09, all detected rearrangements are called. If the CV is between 0.9-0.12, only rearrangement encompassing two or more exons are called. If the value exceeded 0.12 the sample is rejected as not being able to call.

SNP Analysis

SNP sequence database for mapping sequence reads is created by cutting from the whole genome (version 19) sequences of the SNPs with 400 bp flanks around the SNP positions. The combined sequence is indexed for the BWT search and checked for the repetitiveness by counting the number of copies with three or less mismatches for each 100-base segment of the sequence. The SNP probes with multiple occurrences in the genome are excluded from the analysis.

The mapping of the sequence reads to the SNP sequence database is performed by a proprietary program that implements the BWT algorithm. Each sequence read is considered mapped if it matched to the database sequence with 7 or less mismatches.

Sequences reads overlapping a SNP position are used to count the SNP alleles. If both forward and reverse reads of the same clone overlap the SNP position and produce the same allele, only one count is applied for this clone. Clones where the forward and reverse reads produced different alleles are considered a sequencing error and are not counted. Clones with both forward and reverse reads not overlapping the SNP position are counted separately from clones with reads overlapping the SNP position.

The resulting read counts are used to reconstruct allele specific copy number (ASCN) at each SNP location using an algorithm described in Abkevich et al, 2012.

Quality of ASCN Reconstruction

To evaluate the quality of ASCN reconstruction, a quality metric, KS quality, is introduced. Specifically, for each sample, all SNPs are separated in two groups, first group containing all SNPs with allelic imbalance and second group containing all SNPs with equal numbers of copies of the two parental alleles. Allele dosage d at each SNP is transformed as follows: $d_{tr}=d$ if $d<0.5$ and $d_{tr}=1-d$ otherwise. KS quality is defined as $$KS\ quality=sqrt(N_1N_2/(N_1+N_2))max|F_1(d_{tr})-F_2(d_{tr})|$$

where $N_1$ and $N_2$ are the numbers of SNPs in the two groups, $F_1(d_{tr})$ and $F_2(d_{tr})$ are empirical distributions of the transformed allele dosage in the two groups, and maximum is taken over transformed dosage values between 0 and 0.5. In essence, KS quality is measuring how different distributions of transformed dosages between SNPs with balanced and imbalanced alleles. The specific definition of KS quality is based on Kolmogorov-Smirnov statistic. High quality ASCN reconstruction is expected to produce high KS quality. Through visual inspection of about hundred samples, a cutoff value 12.7 for KS quality has been established. ASCN reconstructions with KS quality below this cutoff are considered as failed. There are two major reasons for failures: (1) high noise level in the sequence data and (2) low tumor content in a sample.

Calculation of HRD-LOH, HRD-TAI, and HRD-LST Scores

HRD-LOH score is defined as the number of LOH regions longer than 15 Mb but shorter than the whole chromosome (Abkevich et al, 2012). HRD-LOH score has been shown to be associated with BRCA1, BRCA2, and RAD51C deficiency in 609 ovarian tumors (Abkevich et al, 2012).

HRD-TAI score is defined as the number of regions with allelic imbalance that extend to one of the subtelomeres but do not cross the centromere (Birkbak et al, 2012). A region is counted only if it encompassed a certain minimum number of SNPs (on average approximately 1.8 Mb). We tested for association of HRD-TAI score with BRCA1, BRCA2, and RAD51C deficiency in three datasets of 609 ovarian tumors (data not shown) and found the association to be more significant if the cutoff for the size of HRD-TAI regions is increased to 11 Mb. Therefore, a modified HRD-TAIm score is defined as the number of regions with allelic imbalance that (a) extend to one of the subtelomeres, (b) do not cross the centromere and (c) are longer than 11 Mb.

HRD-LST score is the number of break points between regions longer than 10 Mb after filtering out regions shorter than 3 Mb (Popova et al., 2012). Different cutoffs for HRD-LST score are introduced for "near-diploid" and "near-tetraploid" tumors to separate BRCA1/2 intact and deficient samples. We tested for association of HRD-LST score with BRCA1, BRCA2, and RAD51C deficiency in three datasets of 609 ovarian tumors (data not shown). We also observed that HRD-LST score increases with ploidy both within intact and deficient samples. Instead of using ploidy-specific cutoffs, the HRD-LST score is modified by adjusting it by ploidy:

$$LSTm=LST-kP$$

where P is ploidy and k is a constant. Based on multivariate logistic regression analysis with deficiency as an outcome and HRD-LST and P as predictors, k=15.5 provided the best separation between intact and deficient samples.

Statistical Analysis

All analyses are conducted using R version 3.0.2 (R Core Team, 2013). All reported p values are two-sided. The statistical tools employed in this study include Spearman rank-sum correlation, Kruskal-Wallis one-way analysis of variance, and logistic regression.

For logistic regression modeling, HRD scores and age at diagnosis are coded as numeric variables. Breast cancer stage and subtype are coded as categorical variables. Grade is analyzed as both a numeric and categorical variable, but is categorical unless otherwise noted.

The p values reported for unvariate logistic regression models are based on the partial likelihood ratio. Multivariate p values are based on the partial likelihood ratio for change in deviance from a full model (which includes all relevant predictors) versus a reduced model (which includes all predictors except for the predictor being evaluated, and any interaction terms involving the predictor being evaluated). Odds ratios for RD scores are reported per interquartile range.

I claim:

1. A method of treating a patient with ovarian cancer, comprising administering to the patient (i) an effective amount of ganetespib, or a pharmaceutically acceptable salt thereof; and (ii) an effective amount of cisplatin, wherein the ovarian cancer has been determined to have deficiencies in homologous recombination (HR).

2. The method of claim 1, wherein the ovarian cancer determined to have deficiencies in homologous recombination (HR) has a homologous recombination deficiency (HRD) score of greater than 40.

3. The method of claim 1, wherein the ovarian cancer is epithelial ovarian cancer.

4. The method of claim 1, wherein the ovarian cancer determined to have deficiencies in homologous recombination (HR) has a homologous recombination deficiency (HRD) score of >42.

5. The method of claim 1, wherein the ovarian cancer determined to have deficiencies in HR has a homologous recombination deficiency (HRD) score that is calculated based on loss of heterozygosity (LOH), large scale transitions (LST), and telomeric allelic imbalance (TAI).

6. The method of claim 5, wherein the HRD score is calculated according to the following formula:

$$HRD\text{-model} = 011 \times HRD\text{-}LOH + 0.25 \times HRD\text{-}TAI + 0.12 \times NRD\text{-}LST.$$

7. A method of treating a patient with ovarian cancer, comprising the steps of:
  a) screening the ovarian cancer of the patient to determine that it is HR deficient; and
  b) administering to the patient an effective amount of ganetespib or a pharmaceutically acceptable salt thereof and an effective amount of cisplatin.

* * * * *